(12) United States Patent
Paul

(10) Patent No.: US 8,192,728 B2
(45) Date of Patent: Jun. 5, 2012

(54) METHOD OF TREATING HAIR WITH A SUGAR COMPOSITION

(75) Inventor: Prem Kumar Cheyalazhagan Paul, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 329 days.

(21) Appl. No.: 12/531,084

(22) PCT Filed: Jan. 24, 2008

(86) PCT No.: PCT/EP2008/050822
§ 371 (c)(1),
(2), (4) Date: Jan. 14, 2010

(87) PCT Pub. No.: WO2008/110399
PCT Pub. Date: Sep. 18, 2008

(65) Prior Publication Data
US 2010/0135946 A1    Jun. 3, 2010

(30) Foreign Application Priority Data

Mar. 14, 2007 (EP) .................................. 07104155

(51) Int. Cl.
*A61Q 5/04* (2006.01)
(52) U.S. Cl. ........................................ 424/70.2; 132/211
(58) Field of Classification Search .................... None
See application file for complete search history.

(56) References Cited

U.S. PATENT DOCUMENTS

| | | | |
|---|---|---|---|
| 3,470,887 A | 10/1969 | Kremer | |
| 3,822,238 A | 7/1974 | Blair | |
| 4,156,066 A | 5/1979 | Gould | |
| 4,156,067 A | 5/1979 | Gould | |
| 4,255,550 A | 3/1981 | Gould | |
| 4,354,093 A | 10/1982 | Zago | |
| 4,460,571 A | 7/1984 | Gomez | 424/71 |
| 4,743,673 A | 5/1988 | Johnston | |
| 4,911,919 A | 3/1990 | Patel | |
| 5,000,955 A | 3/1991 | Gould | |
| 5,270,520 A | 12/1993 | Barzilai et al. | |
| 5,507,970 A | 4/1996 | Ishikawa | |
| 5,641,477 A | 6/1997 | Syed | |
| 5,641,480 A | 6/1997 | Vermeer | |
| 5,833,968 A | 11/1998 | Keil | |
| 6,053,178 A | 4/2000 | Todd | |
| 6,384,079 B1 | 5/2002 | Yu et al. | |
| 6,586,378 B2 | 7/2003 | Chandra | |
| 7,988,954 B2 | 8/2011 | Chandra | |
| 2001/0022967 A1 | 9/2001 | Brandt et al. | |
| 2003/0105169 A1 | 6/2003 | Lennon | |
| 2005/0255070 A1 | 11/2005 | Albano | 424/70.14 |
| 2008/0075681 A1 | 3/2008 | Cassier et al. | |
| 2008/0102051 A1 | 5/2008 | Huynh et al. | |
| 2008/0230084 A1 | 9/2008 | Hentrich et al. | |
| 2008/0299147 A1 | 12/2008 | Dillon et al. | |
| 2009/0074697 A1 | 3/2009 | Huynh | |
| 2009/0139537 A1 | 6/2009 | Malle et al. | |

FOREIGN PATENT DOCUMENTS

| | | |
|---|---|---|
| DE | 697 634 | 10/1940 |
| DE | 1201951 | 9/1965 |
| EP | 0455185 A2 | 11/1991 |
| EP | 0530974 A1 | 3/1993 |
| EP | 0619111 A1 | 10/1994 |
| FR | 2899464 | 10/2007 |
| GB | 915816 | 1/1963 |
| GB | 1076420 | 9/1964 |
| JP | 2001-055571 | 2/2001 |
| JP | 2001055571 | 2/2001 |
| JP | 2006232820 | 9/2006 |
| JP | 2006282566 | 10/2006 |
| WO | WO9104007 | 4/1991 |
| WO | WO9500104 | 1/1995 |
| WO | WO0042978 | 7/2000 |
| WO | WO0243675 | 6/2002 |
| WO | WO0243675 A2 | 6/2002 |
| WO | 2004/037217 | 5/2004 |
| WO | WO2004037305 A1 | 5/2004 |
| WO | WO2006061678 A1 | 6/2006 |
| WO | 2006/134409 | 12/2006 |
| WO | WO2008012733 A2 | 1/2008 |

OTHER PUBLICATIONS

Co-pending Application: Applicant: Elliott et al., U.S. Appl. No. 10/592,221, filed Jun. 18, 2007.
PCT International Search Report in PCT application PCT/EP2005/001822; dated Jun. 29, 2005.
PCT International Search Report in PCT application PCT/EP2005/001408; dated Jun. 27, 2005.
Co-pending Application: Applicant: Pye et al., U.S. Appl. No. 12/682,060, filed Sep. 16, 2010.
PCT International Search Report in PCT application PCT/EP2008/063401; dated: Jan. 29, 2009.
Co-pending Application: Applicant: Pye et al., U.S. Appl. No. 12/933,881, filed Oct. 28, 2010.
PCT International Search Report in PCT application PCT/EP2009/053015 dated Jun. 29, 2010.
PCT International Search Report in a PCT application PCT/EP2008/050822.
European Search Report in an EP application EP 07 10 4155.
Cashman, "*Milk minerals (including trace elements) and bone health*", International Dairy Journal, vol. 16, No. 11. (Nov. 2006), pp. 1389-1398.
Abstract of DE 697 634—published Oct. 18, 1940.

*Primary Examiner* — Jyothsna Venkat
(74) *Attorney, Agent, or Firm* — Ronald A. Koatz

(57) ABSTRACT

A hair treatment composition comprising: i) a sugar comprising from three to four waters of crystallisation, esp. lactulose; ii) at least one further ingredient selected from the group consisting of a suitable carrier, a styling polymer or a surfactant.

2 Claims, 1 Drawing Sheet before high humidity (HH)
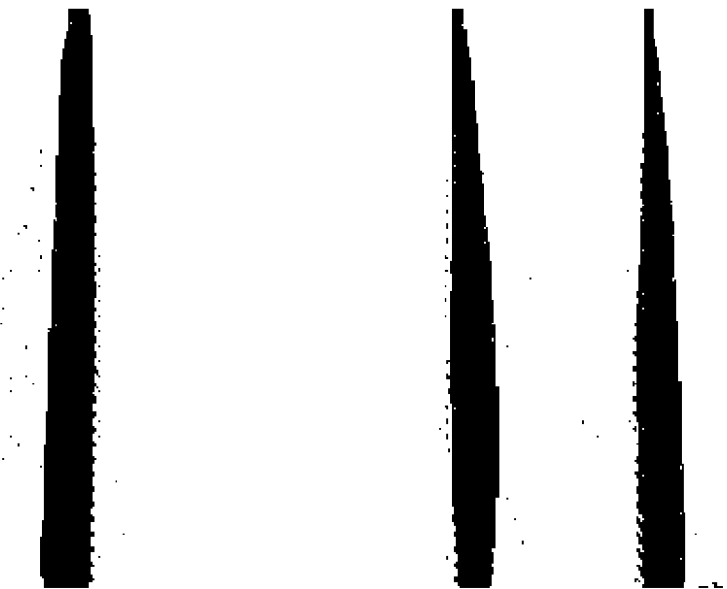
water        2% lactulose
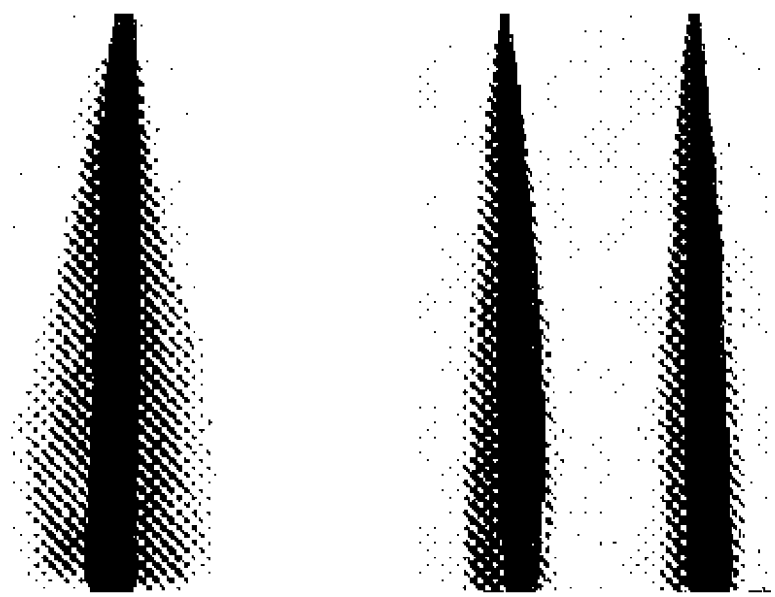
after 3hrs 80%HH

METHOD OF TREATING HAIR WITH A SUGAR COMPOSITION

FIELD OF THE INVENTION

The invention relates to a hair styling compositions and a method of styling. The invention is particularly advantageous in relation to hair straightening.

BACKGROUND AND PRIOR ART

The current hair market has a wide range of styling products. A common way to retain a particular hairstyle is with by applying a hairspray, mousses, gel, lotions or wax. The materials in these compositions are generally film forming agents, resins, gums, and/or adhesive polymers. Good holding power is one attribute a consumer looks for in styling products, as is a natural feel to the hair.

The styling market can be classified in various sub-sets based on the desired styling effect; one such sub-set is products for straightening the hair.

A problem with straightened hair is that once the straightening process has taken place it tends to increase in volume and appear fluffy, this is especially troublesome in humid conditions.

Sugars and sugar derivatives are one class of the countless number of compounds that have been added to hair care compositions.

WO2004/037217 describes heat activated durable styling compositions comprising saccharides and film forming agents.

Clearly, however, not all sugars are the same and not all sugars impart the same properties when applied to a keratinous fibre.

The present invention has now found that compositions containing sugars having three to four waters of crystallisation can be used to impart humidity resistance to straightened hair and thus retain its style.

DETAILED DESCRIPTION OF THE INVENTION

The present invention relates to hair treatment compositions comprising:
i) a sugar comprising from three to four waters of crystallisation; and
ii) at least one further ingredient elected from the group consisting of a suitable carrier, a styling polymer or a surfactant This invention also relates to a method of styling hair comprising the following steps:
i) applying to the hair the composition described above;
ii) heating the hair to a temperature above 100° C.

The invention further relates to the use of a sugar comprising from three to four waters of crystallisation for straightening and imparting humidity resistance to hair.

The Disaccharide

Compositions of the invention comprise a sugar having from three to four waters of crystallisation, preferably three waters of crystallisation.

The sugar is preferably a disaccharide and/or preferably comprises one hexose ring and one pentose ring. Especially preferred is lactulose.

The sugar can be either reducing or non-reducing sugars, however reducing sugars are preferred.

The level of disaccharides present in the total formulation is from 0.05 wt % to 49 wt %, more preferably from 0.2 wt % to 5 wt %, most preferably from 0.5 wt % to 3 wt %.

Styling Compound

In many aspects of this invention it is highly desirable if the composition comprises a styling aid.

Particularly useful as styling aids with this invention are hair styling polymers. Hair styling polymers are well known articles of commerce and many such polymers are available commercially which contain moieties which render the polymers cationic, anionic, amphoteric or nonionic in nature. The polymers may be synthetic or naturally derived.

Styling aids such as vinylic polymer are preferred, in particular block copolymers.

The amount of the hair styling polymer may range from 0.1 to 10%, preferably 0.5 to 8%, more preferably 0.75 to 6% by weight based on total weight of the composition.

Examples of anionic hair styling polymers are:
copolymers of vinyl acetate and crotonic acid;
terpolymers of vinyl acetate, crotonic acid and a vinyl ester of an alpha-branched saturated aliphatic monocarboxylic acid such as vinyl neodecanoate;
copolymers of methyl vinyl ether and maleic anhydride (molar ratio about 1:1) wherein such copolymers are 50% esterified with a saturated alcohol containing from 1 to 4 carbon atoms such as ethanol or butanol;
acrylic copolymers containing acrylic acid or methacrylic acid as the anionic radical-containing moiety with other monomers such as: esters of acrylic or methacrylic acid with one or more saturated alcohols having from 1 to 22 carbon atoms (such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate); glycols having from 1 to 6 carbon atoms (such as hydroxypropyl methacrylate and hydroxyethyl acrylate); styrene; vinyl caprolactam; vinyl acetate; acrylamide; alkyl acrylamides and methacrylamides having 1 to 8 carbon atoms in the alkyl group (such as methacrylamide, t-butyl acrylamide and n-octyl acrylamide); and other compatible unsaturated monomers.

The polymer may also contain grafted silicone, such as polydimethylsiloxane.

Specific examples of suitable anionic hair styling polymers are:
RESYN® 28-2930 available from National Starch (vinyl acetate/crotonic acid/vinyl neodecanoate copolymer);
ULTRAHOLD® 8 available from BASF (CTFA designation Acrylates/acrylamide copolymer);
the GANTREZ®ES series available from ISP corporation (esterified copolymers of methyl vinyl ether and maleic anhydride).

Other suitable anionic hair styling polymers include carboxylated polyurethanes. Carboxylated polyurethane resins are linear, hydroxyl-terminated copolymers having pendant carboxyl groups. They may be ethoxylated and/or propoxylated at least at one terminal end. The carboxyl group can be a carboxylic acid group or an ester group, wherein the alkyl moiety of the ester group contains one to three carbon atoms. The carboxylated polyurethane resin can also be a copolymer of polyvinylpyrrolidone and a polyurethane, having a CTFA designation PVP/polycarbamyl polyglycol ester. Suitable carboxylated polyurethane resins are disclosed in EP-A-0619111 and U.S. Pat. No. 5,000,955. Other suitable hydrophilic polyurethanes are disclosed in U.S. Pat. Nos. 3,822,238; 4,156,066; 4,156,067; 4,255,550; and 4,743,673.

Amphoteric hair styling polymers which can contain cationic groups derived from monomers such as t-butyl aminoethyl methacrylate as well as carboxyl groups derived from monomers such as acrylic acid or methacrylic acid can also be used in the present invention. One specific example of an amphoteric hair styling polymer is Amphomer® (Octylacrylamide/acrylates/butylaminoethyl methacrylate copolymer) sold by the National Starch and Chemical Corporation.

Examples of nonionic hair styling polymers are homopolymers of N-vinylpyrrolidone and copolymers of N-vinylpyrrolidone with compatible nonionic monomers such as vinyl acetate. Nonionic polymers containing N-vinylpyrrolidone in various weight average molecular weights are available commercially from ISP Corporation—specific examples of such materials are homopolymers of N-vinylpyrrolidone having an average molecular weight of about 630,000 sold under the name PVP K-90 and are homopolymers of N-vinylpyrrolidone having an average molecular weight of about 1,000,000 sold under the name of PVP K-120.

Other suitable nonionic hair styling polymers are cross-linked silicone resins or gums. Specific examples include rigid silicone polymers such as those described in EP-A-0240350 and cross-linked silicone gums such as those described in WO 96/31188.

Examples of cationic hair styling polymers are copolymers of amino-functional acrylate monomers such as lower alkyl aminoalkyl acrylate, or methacrylate monomers such as dimethylaminoethyl methacrylate, with compatible monomers such as N-vinylpyrrolidone, vinyl caprolactam, alkyl methacrylates (such as methyl methacrylate and ethyl methacrylate) and alkyl acrylates (such as ethyl acrylate and n-butyl acrylate).

Specific examples of suitable cationic hair styling polymers are:
copolymers of N-vinylpyrrolidone and dimethylaminoethyl methacrylate, available from ISP Corporation as Copolymer 845, Copolymer 937 and Copolymer 958;
copolymers of N-vinylpyrrolidone and dimethylaminopropylacrylamide or methacrylamide, available from ISP Corporation as Styleze® CC10;
copolymers of N-vinylpyrrolidine and dimethylaminoethyl methacrylate;
copolymers of vinylcaprolactam, N-vinylpyrrolidone and dimethylaminoethylmethacrylate;
Polyquaternium-4 (a copolymer of diallyldimonium chloride and hydroxyethylcellulose);
Polyquaternium-11 (formed by the reaction of diethyl sulphate and a copolymer of vinyl pyrrolidone and dimethyl aminoethylmethacrylate), available from ISP as Gafquat® 734, 755 and 755N, and from BASF as Luviquat® PQ11;
Polyquaternium-16 (formed from methylvinylimidazolium chloride and vinylpyrrolidone), available from BASF as Luviquat® FC 370, FC 550, FC 905 and HM-552;
Polyquaternium-46 (prepared by the reaction of vinylcaprolactam and vinylpyrrolidone with methylvinylimidazolium methosulphate), available from BASF as Luviquat®Hold.

Examples of suitable naturally-derived hair styling polymers include shellac, alginates, gelatins, pectins, cellulose derivatives and chitosan or salts and derivatives thereof. Commercially available examples include Kytamer® (ex Amerchol) and Amaze® (ex National Starch).

Also suitable for use as optional components in the compositions of the invention are the ionic copolymers described in WO 93/03703, the polysiloxane-grafted polymers disclosed in WO 93/23446, the silicone-containing polycarboxylic acid copolymers described in WO 95/00106 or WO 95/32703, the thermoplastic elastomeric copolymers described in WO 95/01383, WO 95/06078, WO 95/06079 and WO 95/01384, the silicone grafted adhesive polymers disclosed in WO 95/04518 or WO 95/05800, the silicone macrografted copolymers taught in WO 96/21417, the silicone macromers of WO 96/32918, the adhesive polymers of WO 98/48770 or WO 98/48771 or WO 98/48772 or WO 98/48776, the graft polymers of WO 98/51261 and the grafted copolymers described in WO 98/51755.

With certain of the above-described polymers it may be necessary to neutralise some acidic groups to promote solubility/dispersibility. Examples of suitable neutralising agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanolamine (DIPA); triisopropanolamine (TIPA); and dimethyl stearamine (DMS). A long chain amine neutralising agent such as stearamidopropyl dimethylamine or lauramidopropyl dimethylamine may be employed, as is described in U.S. Pat. No. 4,874,604. Also suitable are inorganic neutralisers, examples of which include sodium hydroxide, potassium hydroxide and borax. Mixtures of any of the above neutralising agents may be used. Amounts of the neutralising agents will range from about 0.001 to about 10% by weight of the total composition.

Product Type

Compositions of the present invention are formulated into hair care compositions, especially products with hair styling claims. The compositions are preferably for use in styling human hair and, more preferably, they are packaged and labeled as such.

It is preferred if the products are left on hair after application and not immediately washed off (within 10 minutes of application).

Preferred product forms are leave on formulations such as gels, mousses, sprays and aerosols.

Further Components

Such styling products frequently include a carrier and further additional components. The carriers and additional components required to formulate such products vary with product type and can be routinely chosen by one skilled in the art. The following is a description of some of these carriers and additional components.

Hair care compositions of the present invention can comprise a carrier, or a mixture of such carriers, which are suitable for application to the hair. The carriers are present at from about 0.5% to about 99.5%, preferably from about 5.0% to about 99.5%, more preferably from about 10.0% to about 98.0%, of the composition. As used herein, the phrase "suitable for application to hair" means that the carrier does not damage or negatively affect the aesthetics of hair or cause irritation to the underlying skin.

Compositions according to the invention comprise a buffer or pH adjuster. Preferred buffers or pH adjusters include weak acids and bases such glycine/sodium hydroxide, citric acid, lactic acid, succinic acid, acetic salt and salts thereof. Frequently a mixture of buffering system is used such as sodium citrate and citric acid.

Carriers suitable for use with hair care compositions of the present invention include, for example, those used in the formulation of hair sprays, mousses, tonics, waters, creams gels, shampoos, conditioners, and rinses. The choice of appropriate carrier will depend on the particular product to be formulated. The carriers used herein can include a wide range of components conventionally used in hair care compositions. The carriers can contain a solvent to dissolve or disperse the styling compound being used, with water, the $C_1$-$C_6$ alcohols, lower alkyl acetate and mixtures thereof being preferred. The carriers can also contain a wide variety of additional materials such as acetone, hydrocarbons (such as isobutane, hexane, decene), halogenated hydrocarbons (such as Freons) and volatile silicones such as cyclomethicone.

When the hair care composition is a hair spray, tonic, gel, or mousse the preferred solvents include water, ethanol, volatile silicone derivatives, and mixtures thereof. The solvents used in such mixtures may be miscible or immiscible with each other. Mousses and aerosol hair sprays can also utilise any of the conventional propellants to deliver the material as a foam (in the case of a mousse) or as a fine, uniform spray (in the case of an aerosol hair spray). Examples of suitable propellants include materials such as trichlorofluoromethane, dichlorodifluoromethane, difluoroethane, dimethylether, propane, n-butane or isobutane. A tonic or hair spray product having a low viscosity may also utilise an emulsifying agent. Examples of suitable emulsifying agents include nonionic, cationic, anionic surfactants, or mixtures thereof. If such an emulsifying agent is used, it is preferably present at a level of from about 0.01% to about 7.5% by weight based on total weight of the composition. The level of propellant can be adjusted as desired but is generally from about 3% to about 30% by weight based on total weight for mousse compositions and from about 15% to about 50% by weight based on total weight for aerosol hair spray compositions.

Hair styling creams or gels also typically contain a structurant or thickener, typically in an amount of from 0.01% to 10% by weight.

Suitable spray containers are well known in the art and include conventional, non-aerosol pump sprays i.e., "atomisers", aerosol containers or cans having propellant, as described above, and also pump aerosol containers utilising compressed air as the propellant.

The formulation may include conditioning materials such as surfactants, cationic conditioners suitable for hair, quaternary silicone polymers, silicone based conditioners and their emulsions, and amino functional silicones and their emulsions.

Further general ingredients suitable for all product forms include, sun-screening agents, anti-dandruff actives, carboxylic acid polymer thickeners for hair shampoo and conditioner compositions and emulsifiers for emulsifying the various carrier components of the compositions of the invention.

The compositions of the present invention may also contain adjuncts suitable for hair care. Generally such ingredients are included individually at a level of up to 2, preferably up to 1 wt % of the total composition. Suitable hair care adjuncts, include amino acids, sugars and ceramides.

The method of the invention comprises applying compositions of the invention followed by a heating step. The hair should be heated to a temperature above 100° C., preferably above 150° C., more preferably above 180° C.

The following non-limiting Examples further illustrate the preferred embodiments of the invention. All percentages referred to in the examples and throughout this specification are by weight based on total weight unless otherwise indicated.

EXAMPLES

Hair switches were soaked in 2% sugar solutions solution for 1 hour and styled straight using wet to dry hot irons. After the final iron pass the switches were combed at least 5 times. This was to reduce or eliminate possible surface effects of sticky sugars.

The switches were left for 3 hours at 30° C. and 80% relative humidity.

TABLE 1

| Sugar | Final volume (mm$^2$) after 3 hrs at 80% rH |
| --- | --- |
| no sugar - water | 13795 |
| sucrose | 10752 |
| cellobiose | 12203 |
| sucralose | 11475 |
| lactulose | 7699 |

Table 1 demonstrates that lactulose has significant straightening and anti-humidity and styling benefits compared to water and alternative sugars.

FIG. 1 demonstrates the anti-humidity benefits when 0.5 grams of 2% lactulose solution (aqueous base) was sprayed onto hair.

The invention claimed is:

1. A method of styling hair comprising applying to the hair a composition consisting of:
   0.5 to 3 wt % of lactulose and
   heating the hair to a temperature above 100° C.
2. A method according to claim 1, in which the hair is heated to a temperature above 150° C.

* * * * *